United States Patent [19]

Iwatschenko et al.

[11] 4,355,638

[45] Oct. 26, 1982

[54] INFUSION APPARATUS

[75] Inventors: Peter Iwatschenko, Neunkirchen, Fed. Rep. of Germany; Josef Hirschmann, Fliederstr. 2a, 8021 Neuried, Fed. Rep. of Germany

[73] Assignee: Josef Hirschmann, Fed. Rep. of Germany

[21] Appl. No.: 100,513

[22] Filed: Dec. 5, 1979

[30] Foreign Application Priority Data

Dec. 8, 1978 [DE] Fed. Rep. of Germany ....... 2853200

[51] Int. Cl.³ .............................................. A61M 5/00
[52] U.S. Cl. ......................... 128/214 F; 128/DIG. 12; 417/477
[58] Field of Search ............... 128/214, 214 E, 214 F, 128/DIG. 12, DIG. 13; 417/478–480

[56] References Cited

U.S. PATENT DOCUMENTS

| | | | |
|---|---|---|---|
| 3,349,716 | 10/1967 | Weber | 417/478 |
| 3,985,133 | 10/1976 | Jenkins et al. | 128/214 F |
| 3,990,444 | 11/1976 | Vial | 128/214 F |
| 4,014,318 | 3/1977 | Dockum et al. | 417/479 |
| 4,155,362 | 5/1979 | Jess | 128/214 F |
| 4,184,815 | 1/1980 | Casson et al. | 128/214 F |

*Primary Examiner*—Stephen C. Pellegrino
*Attorney, Agent, or Firm*—Ostrolenk, Faber, Gerb & Soffen

[57] ABSTRACT

The disclosure concerns a gravity operated infusion apparatus. A solvent container is suspended above an infusion needle. A flexible tube joins the container and needle. A tube clamp varies the cross-section of the tube for controlling the infusion rate. Between the tube clamp and the needle an additional pressing apparatus is selectively actuable for increasing the pressure within the tube and between the tube clamp and infusion needle. In one embodiment the pressing apparatus comprises an eccentric disc that cooperates with a plate for pressing the tube and in another embodiment two plates are squeezed together against the tube. In a modification embodiment one plate rocks or tumbles as it moves with respect to the other plate.

20 Claims, 5 Drawing Figures

INFUSION APPARATUS

The invention relates to an infusion apparatus operating by the gravity principle and comprising a solvent container which is suspended at a higher level than the infusion point and to which a drop chamber is connected which is connected via an infusion flexible tube to an infusion needle, and a tube clamp for varying the cross-section of the flexible tube for controlling the infusion rate.

In gravity infusion the pressure for the solution to be infused is produced by the weight of the solution itself. In practice, this is effected by suspending the solvent container higher than the infusion point with the infusion cannula. The pressure produced or increased by gravity of about 0.15 bar = 1500 mm water column overcomes the counter pressure of the body of about 80 mm water column and infuses the fluid. The magnitude of the pressure depends on the height of suspension of the solvent container.

When the fluid in the solvent container is nearly exhausted and the pressure in the fluid drops to the counter pressure of the body, the infusion ceases. A liquid column corresponding to the body counter pressure remains to ensure that no air is infused.

The infusion rate is adjusted in the simplest manner with a tube clamp or, when higher demands are made, with a control means for controlling the infusion rate which also effects a compression and reduction of the cross-section of the infusion tube.

Due to the principle of producing the pressure necessary for the infusion by gravity, in the aforementioned manner it is not possible for an inadmissibly high pressure to arise and on the other hand the pressure drops automatically when the supply of infusion solution approaches its end and air enters the infusion fittings.

For special applications, for example infusions into the thin blood vessels of children, infusion with elevated pressure is however necessary. Ordinary pump means cannot be used for this purpose because there is a danger that air will be infused when the solvent container is emptied.

The problem underlying the invention is to provide an infusion apparatus of the type mentioned at the beginning with which it is possible to increase the infusion pressure without any danger of infusion of air.

This problem is solved by the invention set forth in claim 1.

Further advantageous developments and embodiments of the invention are apparent from the subsidiary claims.

The construction of the infusion apparatus according to the invention makes it possible to increase the infusion pressure without any danger of the infusion of air because in the infusion flexible tube only periodic pressure fluctuations are produced which with a tube filled with air can readily compensate each other so that when an air column occurs between infusion point and pressing means there is still an adequate fluid column before the infusion point.

An advantageous application of the infusion apparatus according to the invention is in conjunction with control means which are adjustable to a desired infusion rate and which open a tube clamp to a varying degree in dependence upon the number of drops falling through the drop chamber. If when using such control infusion means blockage of the infusion needle or constriction of its effective cross-section occurs, the control means adjusts the tube clamp to the largest opening and then detects that even in this position of the clamp no drop passes through. The control means may be so constructed that when this condition occurs, which is an alarm condition, said means completely closes the tube clamp and drives the control means of the pressing means so that pressure fluctuations are produced thereby in the liquid column between the tube clamp and the infusion needle which in most cases remove stoppages or constrictions of the outlet cross-section. The pressure generation may preferably be in several stages, for example three. The tube portion is compressed to various extents, although even at full pressure generation a fluid passage remains for pressure compensation. These three stages of the compression can be produced successively, the tube clamp being reopened after each stage and a determination made whether a drop falls in the drop chamber in appropriate time.

If the check result is negative the control means switches the pressing means to the next highest stage of the pressure generation whereas if it is positive the control means can switch back to the next-lowest stage.

Thus, with brief closures of the infusion channel the entire infusion apparatus thereafter automatically returns to gravity operation but oscillates permanently between the various pressure generation stages when permanent pressure support is necessary to obtain the desired infusion rate.

The invention will be explained hereinafter with reference to the examples of embodiment illustrated in the drawings, wherein.

Figure 1:
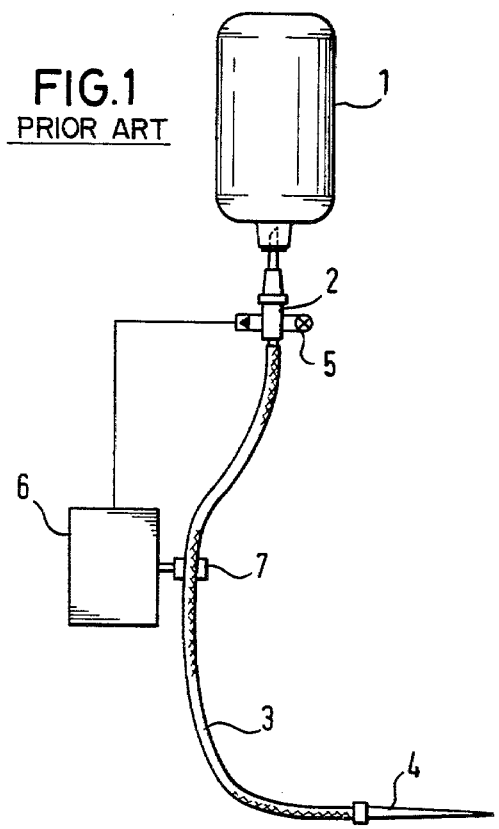
FIG. 1 shows a known embodiment of an infusion apparatus operating by the gravity principle.

FIG. 1 illustrates a known infusion apparatus operating by the gravity principle. This infusion apparatus comprises a solvent container 1, a drop chamber 2, an infusion flexible tube 3 and an infusion needle 4. This infusion apparatus is also provided with a control means for regulating the infusion rate which includes a drop sensor 5 and a tube clamp 7 controlled via an electronic control means 6. The cross-section of the tube 3 in the region of the clamp 7 is adjusted to the desired value by the control means 6 in dependence upon the drops falling through the drop chamber 2.

In simpler infusion means of this type the tube clamp 7 is adjusted manually to a value obtained empirically or by experience.

However, with temporary high counter pressure at the infusion point or in the case of infusion into very narrow blood vessels falling of the drop through the drop chamber 2 can be prevented. To obviate this disadvantage, in the embodiment illustrated in FIG. 2 a pressing means 9 is provided which permits compression of the tube between the tube clamp 7 and the infusion point 4 so that in this region of the tube the pressure is increased. In the normal case, the infusion means operates with the pessure generated by gravity. However, if this pressure is not adequate the pressing means 9 with the aid of the control means 8, either by manual control or controlled by a usual control means 6, can produce individual or periodic pressure fluctuations in the region of the tube between the clamp 7 and the infusion needle 4. For this reason, in the region of the tube 3 between the drop chamber 2 and the pressing means 9 either a check valve may be provided or a means reducing the cross-section of the tube; alternatively, the clamp 7 actuated by the control means 6 can be utilized for this purpose. For independent operation without a control means 6 the pressing means 9 can be periodically compressed by the control means 8 so that a pulsating pressure oscillation of the liquid column results in the infusion tube, the fluid thereby being conveyed out of the solvent container to the patient.

When the control means 6 are employed, said means determine with the aid of a drop sensor 5 whether or not a drop falls in the drop chamber. The tube clamp 7 is opened by said control means to a varying degree in dependence upon the desired number of drops per unit time and thus the infusion rate. If due to stoppage or constriction of the infusion channel no drops or inadequate drops per unit time fall through the drop chamber the control means 6 drives the control means 8 and the portion of the tube in the pressing means 9 is thereby compressed, the resulting pressure increase causing the infusion fluid to emerge through the infusion needle 4. Before compression of the tube the control means 6 acts on the clamp 7 so that the cross-section of the tube is greatly reduced at least in the region of said clamp 7, if not closed completely.

As long as fluid is present in the tube 3 the compression of the tube portion in the pressing means 9 produces excess pressure in the system which however is limited by the elasticity of the tube. If air enters the system, it can be compressed and the pressure rises only slightly. By dimensioning the pressing means, in particular the length of the portion of the tube compressed by the pressing means 9 between the clamp 7 and the infusion needle 4, the maximum pressure which arises when air enters the system is fixed. The pressure can thus be limited so that it definitely remains below the body counter pressure and air infusion is impossible.

The maximum pressure arising in the flexible tube 3 is limited either by elasticity of the tube or by limiting the force on the pressing means 9.

The pressing means 9 is controlled in dependence upon the number of drops falling through the drop chamber 2 and the position of the clamps 7 and infusion amount to be delivered.

Examples of embodiment of the pressing means are explained hereinafter with reference to FIGS. 3 through 5.

Figure 3:
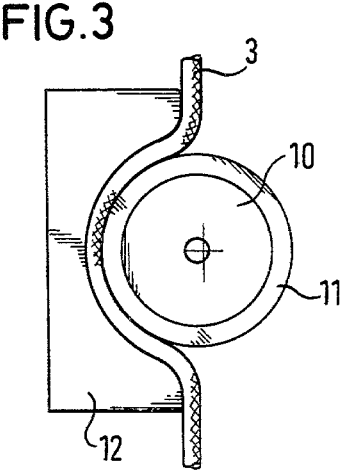
FIG. 3 shows an embodiment of the pressing means for increasing the pressure.

The embodiment of the pressing means illustrated in FIG. 3 consists of a substantially circular concave support plate 12 on which the portion of the tube rests, an eccentric disc 10 pressing via a slide ring 11 on said tube portion. By adjustment of the distance between the plate 12 and the axis of the eccentric disc 10 adjustment of the maximum pressure increase is possible and the speed of rotation of the eccentric disc 10 driven by rotating motor means (not shown) determines the frequency of the pressure fluctuations per unit time. With continuous rotation of the eccentric in this manner periodic pressure fluctuations may be obtained in the liquid column.

Figure 4:
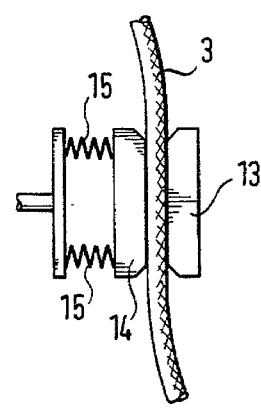
FIG. 4 shows a further embodiment of a pressing means for increasing the pressure.

In the embodiment of the pressing means in FIG. 4 the portion of the tube 3 disposed between two plates 13, 14 and the plate designated by 14 can be pressed via springs 15 with the aid of a drive means not shown against the plate 13 to compress the tube. The drive means in this case can be formed by an electromagnet or an electric motor. The force is limited by the spring elements 5 at the pressure jaws or by limiting the power of the drive member. Further limitation results from the elasticity of the tube as described above.

Figure 2:
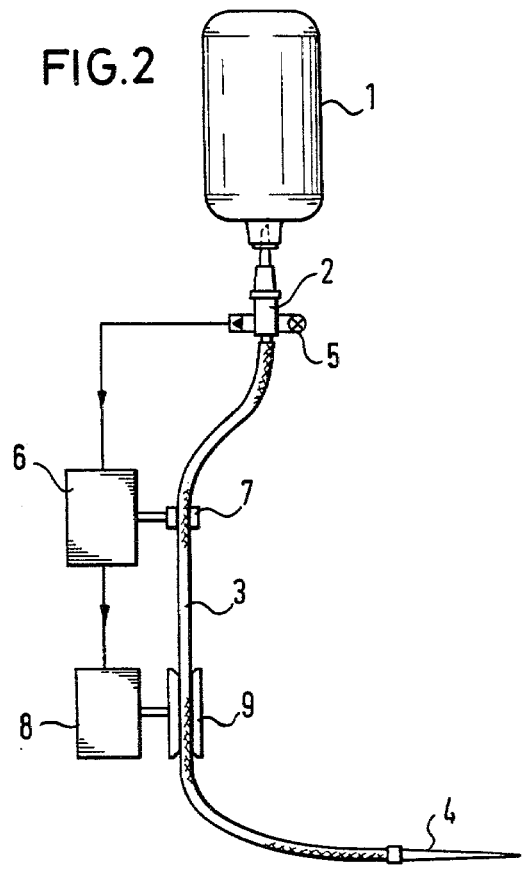
FIG. 2 shows an embodiment of the infusion apparatus according to the invention.
Figure 5:
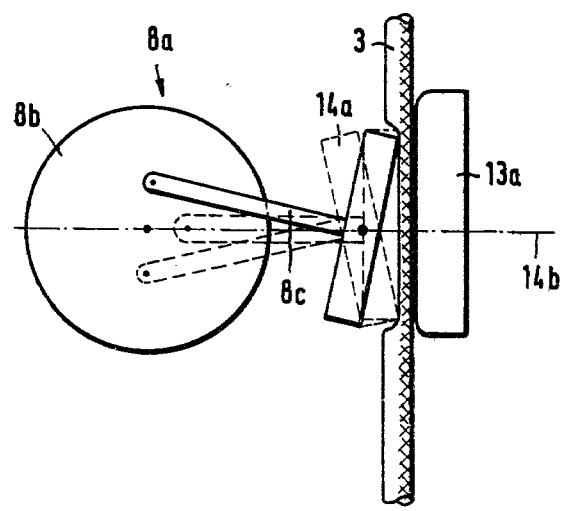
FIG. 5 shows a third embodiment of a pressing means for increasing the pressure.

FIG. 5 shows an embodiment of the pressing means which is similar to the embodiment of FIG. 4, but wherein one plate 14a is subjected to a tumbling movement by means of a mechanism 8a which forms part of the control means 8 shown in FIG. 2; The mechanism 8a includes a crank disc (8b) which may selectively be driven into rotation by motor means not shown and drives a connecting rod 8c which is rigidly connected to plate 14a at the center thereof. The center of plate 14a further is guided along to dashed straight line 14b perpendicular to the plane of the front surface of plate 13a in contact with the tube 3. Therefore plate 14a performs a tumbling movement wherein at a first instant only the upper half of the plate comes into contact with the tube 3 compressing it to a continuously greater extent until plate 14a is parallel to plate 13a. Thereupon the upper half of plate 14a moves from tube 3 leaving the lower half of plate 14a in engagement with tube 3. Finally plate 14a is completely withdrawn from tube 3.

By the tumbling movement of plate 14a a soft and continuous increase of the pressure within tube 3 is obtained. The mechanism 8a of course may be replaced by other mechanism known in the art for obtaining said tumbling movement. Of course, other embodiments of the processing means are conceivable because the only important point is that a certain portion of the tube is briefly or periodically compressed. Furthermore, it is not necessary for the tube 3 to form a continuous part with the compressed portion; said portion can firstly consist of material different to that of the remaining tube 3, for example of silicone rubber, and secondly said portion may have a different cross-sectional form or different cross-sectional area than the remaining tube 3, depending on the desired pressure increase.

It is further possible to make the compressed tube portion as separate portion which is connected to the actual infusion tube 3 via a branching.

When using the pressing means 9 and the associated control means 8 in conjunction with an infusion system having a control means 6 according to FIG. 2 the pressure may be generated in a plurality, for example three, of stages, in each of which the tube portion is compressed to a different extent. Even with full pressure generation a fluid passage remains in the tube portion at the compressed point for pressure compensation.

If the control means 6 establishes that support pressure is required the clamp 7 is closed. Thereafter, the pressing means 9 is driven with the aid of the control means 8 so that the first stage of compression of the tube portion results, whereupon the pressing means returns to the starting or rest position. The control means 6 then again checks by opening the clamp 7 whether infusion fluid can flow. If this is not the case, the next stage of compression of the tube portion is initiated. Thereafter, a check is again made whether fluid can flow. If the result of this check by the control means is negative, i.e. adequate dripping in the drop chamber is not detected or there is no output signal from the drop sensor, the next highest stage of the pressing means 8 is switched on. If the check remains negative even with the highest pressure stage the apparatus initiates an alarm.

If with the aid of the drop sensor 5 the control means 6 detects that drops are falling through the drop chamber and solution thus flowing, it switches back one stage in the following pressure support of the pressing means 8. Consequently, in the case of brief closures of the infusion passage the system automatically returns to pure gravity operation. When pressure support is continuously necessary, however, the system permanently oscillates between the stages of the pressing means 9.

The embodiments of the pressing means illustrated in FIGS. 3 through 5 represent only advantageous ones.

Further advantageous embodiments can be obtained by using magnetostrictive or electrostrictive elements for the plates 13, 14 or the plate 12 and the slide ring 11. In this case, the electric motor or electromagnetic drive may be omitted so that no mechanically driven elements are necessary.

We claim:

1. Infusion apparatus operable by gravity, and comprising:
   a solvent container for being suspended at a higher level than the infusion point; a drop chamber means beneath the container and connected to the container for infusion to drop through;
   an infusion needle; an infusion tube connecting the drop chamber means and the needle, the infusion tube being clampable for changing the cross-section thereof;
   a tube clamp means connected on the tube for clamping the tube to vary the cross-section thereof to a selected cross-section for controlling the normal gravity flow infusion rate;
   pressure increasing means connected externally of the tube at a portion of the tube between the tube clamp means and the needle; the pressure increasing means being selectively actuated in response to predetermined flow conditions in said tube for periodically increasing the pressure in the section of the tube between the tube clamp means and the needle and for thereafter permitting the pressure in that section of the tube to decrease by compressing and then releasing the tube at spaced time intervals.

2. The infusion apparatus of claim 1, wherein at the portion of the tube at the pressure increasing means, the tube is resiliently formed and the pressure-increasing means comprises pressing means for controllably compressing the tube portion for producing pressure fluctuations in the tube.

3. Infusion apparatus operable by gravity, and comprising:
   a solvent container for being suspended at a higher level than the infusion point; a drop chamber means beneath the container and connected to the container for infusion to drop through;
   an infusion needle; an infusion tube connecting the drop chamber means and the needle, the infusion tube being clampable for changing the cross-section thereof;
   a tube clamp means connected on the tube for clamping the tube to vary the cross-section thereof to a selected cross-section for controlling the normal gravity flow infusion rate;
   pressure increasing means connected externally of the tube at a portion of the tube between the tube clamp means and the needle; the pressure increasing means being selectively actuated in response to predetermined flow conditions in said tube for periodically increasing the pressure in the section of the tube between the tube clamp means and the needle and for thereafter permitting the pressure in that section of the tube to decrease by compressing and then releasing the tube at spaced time intervals;
   at the portion of the tube at the pressure increasing means, said tube being resiliently formed and the pressure increasing means comprising pressing means for controllably compressing the tube portion for producing pressure fluctuations in the tube;
   said pressing means comprising two plates between which the tube portion passes;
   and means for driving the plates toward and away from one another for selectively compressing and then releasing the tube at spaced time intervals.

4. The infusion apparatus of claim 2, wherein the plates are oriented parallel to each other and the driving means drive the plates toward and away from one another generally along a direction perpendicular to the planes of the plates.

5. The infusion apparatus of either of claims 3 or 4, wherein the frequency of the driving movement of the plates toward one another is variable for varying the time under which the tube is pressurized.

6. The infusion apparatus of either of claims 3 or 4, wherein the amplitude of the driving movement of the plates toward one another is variable for varying the pressure in the tube.

7. The infusion apparatus of claim 3, wherein the plates connected to the drive means are interchangeable for others of the plates that are sized for contacting a different size area of the tube.

8. The infusion apparatus of claim 3, wherein the drive means for the plates comprises an electromagnet drive means.

9. The infusion apparatus of claim 3, wherein the drive means for the plates comprises an electric motor connected with the plates for moving the plates toward and away from one another.

10. The infusion apparatus of either of claims 2 or 3, wherein the tube portion contacted by the pressure increasing means is comprised of silicone rubber, and the remainder of the tube is comprised of a PVC flexible tube; and the silicone rubber and PVC portions of the tube are of the same cross-section.

11. The infusion apparatus of either of claims 2 or 3, wherein the tube portion contacted by the pressing means is of a different cross-section than the remainder of the tube.

12. The infusion apparatus of claim 3, wherein the tube portion for being contacted by the pressing means is separate from the infusion tube and is connected with the infusion tube by a branch member.

13. The infusion apparatus of either claims 1 or 3, further comprising means for constricting the cross-section of the tube and located between the pressure increasing means and the drop chamber.

14. The infusion apparatus of either claims 1 or 3, further comprising a detector for measuring the rate of infusion of the tube and the detector generating an output signal; means connecting that output signal to the pressure increasing means for controlling the pressure increasing means.

15. The infusion apparatus of either of claims 1 or 3, wherein the pressure increasing means operates to produce cyclic pressure fluctuations.

16. The infusion apparatus of any of claims 1, 2 or 3, wherein the tube between the pressure increasing means and the needle is opened for not blocking return of any fluid in the tube in the direction past the pressure increasing means toward the tube clamp upon the pressure increasing means selectively not applying pressure to the tube portion.

17. The infusion apparatus of claim 14, wherein the tube between the pressure increasing means and the needle is opened for not blocking return of any fluid in the tube in the direction past the pressure increasing means toward the tube clamp upon the pressure increasing means selectively not applying pressure of the tube portion.

18. The infusion apparatus of claim 1 or 2, wherein the pressure increasing means is formed by pressing means controllably compressing a resiliently formed portion of the tube for producing pressure fluctuations in the tube, said pressing means being formed by a substantially circular concave support plate on which said portion of said tube bears and opposite said tube there is an eccentric means which presses said portion of said tube against the plate.

19. The infusion apparatus of claim 18, wherein the eccentric means is formed by an eccentrically mounted roller means on the outer periphery of which a slide ring is disposed, and wherein the latter is rotatable with respect to the eccentrically mounted roller means and presses the tube portion against the plate.

20. The infusion apparatus of claim 1, wherein the pressing apparatus is formed by two plates between which said portion of said tube is passed, at least one of said plates being driveable towards the other of said plates, and said at least one of said plates performs a tumbling movement relative to said other of said plates and in the direction towards said other of said plates.

* * * * *